US009617326B2

(12) United States Patent
Chen et al.

(10) Patent No.: US 9,617,326 B2
(45) Date of Patent: Apr. 11, 2017

(54) RTRAIL MUTANT AND MONOMETHYL AURISTATIN E CONJUGATE THEREOF

(71) Applicant: Zhejiang University, Hangzhou, Zhejiang (CN)

(72) Inventors: Shuqing Chen, Hangzhou (CN); Liqiang Pan, Hangzhou (CN)

(73) Assignee: Zhejiang University, Hangzhou, Zhejiang (CN)

( * ) Notice: Subject to any disclaimer, the term of this patent is extended or adjusted under 35 U.S.C. 154(b) by 95 days.

(21) Appl. No.: 14/437,987

(22) PCT Filed: Jun. 20, 2013

(86) PCT No.: PCT/CN2013/077566
§ 371 (c)(1),
(2) Date: Apr. 23, 2015

(87) PCT Pub. No.: WO2014/063495
PCT Pub. Date: May 1, 2014

(65) Prior Publication Data
US 2015/0307587 A1 Oct. 29, 2015

(30) Foreign Application Priority Data
Oct. 25, 2012 (CN) .......................... 2012 1 0416648

(51) Int. Cl.
*C07K 14/52* (2006.01)
*C12N 15/19* (2006.01)
(Continued)

(52) U.S. Cl.
CPC ...... *C07K 14/70575* (2013.01); *A61K 38/177* (2013.01); *A61K 47/48246* (2013.01); *A61K 47/48338* (2013.01); *A61K 38/00* (2013.01)

(58) Field of Classification Search
None
See application file for complete search history.

(56) References Cited

U.S. PATENT DOCUMENTS

2004/0186051 A1* 9/2004 Kelley ................ C07K 14/525
2011/0070248 A1 3/2011 Ichikawa et al.

FOREIGN PATENT DOCUMENTS

| CN | 1354183 A | 6/2002 |
| CN | 1436792 A | 8/2003 |

(Continued)

OTHER PUBLICATIONS

NCI Thesaurus, Gene (Code C16612), [online] Version 16.08e (Release date:Aug. 29, 2016) [retrieved on Sep. 20, 2016]. Retrieved from the Internet: <URL: https://ncit.nci.nih.gov/ncitbrowser/ConceptReport.jsp?dictionary=NCI_Thesaurus&version=16.08e&ns=NCI_Thesaurus&code=C16612>.*

(Continued)

*Primary Examiner* — Claire Kaufman
(74) *Attorney, Agent, or Firm* — Bret E. Field; Bozicevic, Field & Francis LLP (57) ABSTRACT

Disclosed are an rTRAIL mutant and monomethyl auristatin E (MMAE) conjugate thereof. The amino acid sequence thereof is as represented by SEQ ID No.1. Also disclosed are a coding gene of the rTRAIL mutant and expression system, recombinant vector and expression unit containing the coding gene. Also disclosed are an rTRAIL mutant-vcMMAE conjugate and preparation and uses thereof. The conjugate of the present invention has the biological functions of both the rTRAIL mutant and the MMAE; the MMAE is directionally transferred to a tumor cell through the specific binding between the rTRAIL mutant and a death receptor on the surface of the tumor cell, and is released and takes effect in the tumor cell, thus killing the tumor cells less sensitive or even resistant to TRAIL, and reducing the toxicity generated by the separate administration of the MMAE.

9 Claims, 4 Drawing Sheets

(51) Int. Cl.
*C12N 15/10* (2006.01)
*C07K 14/705* (2006.01)
*A61K 47/48* (2006.01)
*A61K 38/17* (2006.01)
*A61K 38/00* (2006.01)

(56) References Cited

FOREIGN PATENT DOCUMENTS

| CN | 102388062 A | 3/2012 |
| CN | 102936281 A | 2/2013 |
| KR | 10-2006-0113496 A | 11/2006 |
| WO | WO03043583 A2 | 5/2003 |
| WO | WO2007063301 A1 | 6/2007 |

OTHER PUBLICATIONS

Pan et al., Novel conjugation of tumor-necrosis-factor-related apoptosis-inducing ligand (TRAIL) with monomethyl auristatin E for efficient antitumor drug delivery, Adv Mater. Sep. 14, 2013;25(34):4718-4722.

* cited by examiner

RTRAIL MUTANT AND MONOMETHYL AURISTATIN E CONJUGATE THEREOF

FIELD OF THE INVENTION

The prevent invention relates to the field of both biotechnology and medicine, in particular to an rTRAIL mutant and its monomethyl auristatin E (MMAE) conjugate.

BACKGROUND OF THE INVENTION

Tumor necrosis factor (TNF) related apoptosis-inducing ligand (TRAIL, or Apo2L or TNFSF10) is the third apoptosis factor in the TNF family found after TNF and FasL, and is believed to be a promising anticancer biological medicine. TRAIL was cloned from myocardial cDNA library by Wiley et al., and was named not only because its amino acid sequence had the structure characteristics of the TNF superfamily, but also because it is capable of inducing apoptosis of Jurkat cells and EB virus-transformed human lymphocytes. TRAIL belongs to type II transmembrane protein and is composed of 281 amino acids. Its N terminal ($1^{st}$-$17^{th}$ amino acids) is located inside the cell and its C terminal ($39^{th}$-$281^{st}$ amino acids) extends outside the cell, wherein the $114^{th}$-$281^{st}$ amino acids play the main function.

A lot of preclinical researches have shown that TRAIL is capable of inducing apoptosis of various types of cancer cell lines with no side effects on normal cells. By now, phase I and II clinical trials of TRAIL and its receptor-agonist antibody have been conducted abroad, and preliminary efficacy has been achieved. Besides, TRAIL only exhibits very weak activation effect on NF-κB, therefore, even being administered systematically, it will not induce severe inflammatory response just as that produced by TNF-α and Fas-L. As a result of this, TRAIL has potential to develop into a new generation of anti-tumor medicine.

Located on cell membrane, TRAIL is expressed in the cells of immune system, including the NK cell, T cell, macrophage and dendritic cell, which can be processed into a soluble form by cysteine protease. TRAIL plays an apoptosis—inducing role by binding with its cell membrane receptors. Up to now, 5 kinds of TRAIL receptors have been found, including TRAIL-R1 (DR4, TNFSF10a) and TRAIL-R2 (DR5, TNFRSF10b); TRAIL-R3 (DcR1, TNFRSF10c) and TRAIL-R4 (DcR2, TNFRSF10d); and circulating osteoprotegerin (OPG, TNFRSF11b). DR4 and DR5 have a segment of death domain (DD), which is indispensable for inducing apoptosis after TRAIL binds with the receptors. Due to lack of functional death domain (DD), other 3 receptors, although being capable of binding with TRAIL, cannot induce apoptosis.

Binding of TRAIL with DR4 or DR5 may activate both mitochondrial-dependent and non mitochondrial-dependent apoptosis signaling pathways, mediate death signal to be transmitted into the cells, initiate the effector Caspase-3, and eventually induce tumor cell apoptosis.

Recently, it has been found that recombinant soluble TRAIL induces apoptosis of a broad spectrum of human tumor cell lines. However, there are still certain of tumor cells with low sensitivity or resistance to TRAIL, e.g., all the human melanoma cell lines, most breast cancer cell lines, prostate cancer cell line LNcaP and the like. Although DR4 or DR5 is more or less expressed on the surface of these cells, binding of TRAIL with DR4 or DR5 cannot induce the final apoptosis of the cells because of the absent or mutation of the key enzyme involved in the apoptosis pathway of the cells and the high expression level of other apoptosis inhibiting proteins.

For the solid tumor formed by these cells, alternative therapeutic means are needed urgently, or, other aspects, e.g., modifying TRAIL to make it able to kill the tumor cells with low sensitivity or resistance, are also need. As shown in studies, combined use of soluble recombinant TRAIL (rTRAIL) with radiotherapy and chemotherapy may increase sensitivity of tumor cells to rTRAIL, i.e., the two display a synergistic effect. Now, the internationally applied rTRAIL is the fragment of the $95^{th}$-$281^{st}$ amino acids. The rTRAIL monomer tends to form into a trimer having better biological activity, the top of which has a binding site of zinc ion that plays an important role on stabilizing the trimer's conformation.

Combined treatment protocol just includes administrating rTRAIL with these drugs simultaneously, but the link between them has not been set up, resulting in the failure of transporting these drugs to the tumor cells directionally. Thus, only drugs with low-dose and low-toxicity are usually selected, so as to prevent normal cells from damage. Accordingly, better efficacy cannot be achieved. Efficient utilization of strong tumor cell-killing drugs would be more helpful for tumor therapy. For example, MMAE (Monomethyl auristatin E), known as a chemotherapeutic drug, is a synthetic anti-tumor small molecule, which induces apoptosis by inhibiting dimerization of tubulin in cells. However, due to its highly unspecific toxicity, MMAE can damage normal cells. Hence, it is impossible for MMAE itself to be developed into a medicine. Besides, the studies on mutants of TRAIL and antibodies of TRAIL receptors are still in progress, but the efficacy thereof is not satisfactory.

SUMMARY OF THE INVENTION

The objective of the present invention is to provide an rTRAIL mutant, in which a specific amino acid is mutated into a cysteine, such that the conjugation with MMAE is achieved and the tumor cell-killing ability of the protein will not be significantly reduced.

In one aspect, the present invention provides an rTRAIL mutant, of which the amino acid sequence is represented by SEQ ID No.1.

Said mutant is taken from the $95^{th}$-$281^{st}$ amino acids within the full-length amino acid sequence of TRAIL protein, and the $109^{th}$ asparagine (Asn) is mutated into a cysteine (Cys).

In another aspect, the present invention provides a gene encoding the rTRAIL mutant, of which the base sequence is represented by SEQ ID NO.2. The codon AAT of the $109^{th}$ Asn is mutated into TGT, the codon of Cys.

In another aspect, the present invention provides an expression unit, a recombinant vector or an expression system containing said gene.

The promoter of said expression unit is T7. Under the action of the promoters, rTRAIL mutant can directly achieve intracellularly soluble expression in *Escherichia coli* (*E. coli*) host cells.

The original vector of said recombinant vector is pET-28a(+).

Said expression system may be selected from bacterium, yeast, insect cell or mammalian cell expression system, preferably the bacterium expression system, most preferably the *E. coli* expression system.

In another aspect, the present invention provides an rTRAIL mutant-MMAE conjugate, which is formed by conjugating MMAE with rTRAIL mutant trimer through a linker. The synthetic method of said MMAE has been documented in a US patent literature (U.S. Pat. No. 5,635, 483, Tumer inhibiting tetrapeptide bearing modified phenethyl amides).

Said linker used in the present invention is a maleimide-modified valine-citrulline dipeptide, which can be synthetized by the method described in Gene M. D., et al, Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity, *Bioconjugate Chem.*, 13(4) 855-869 (2002).

The MMAE with the linker of the present invention (vcMMAE) may be synthesized either by entrusting Jiangyin Concortis Biotechnology Co., Ltd, or by referring to literatures (See Svetlana O. D., et al, Development of potent monoclonal antibody auristatin conjugates for cancer therapy [J], Nature Biotechnology., 21(7) 778-784 (2003).). When being conjugated, an alkylation reaction is performed between the maleimide on valine and the cysteine sulfhydryl group of the rTRAIL mutant to obtain the conjugate of the present invention eventually.

In another aspect, the present invention provides a preparation method for said rTRAIL mutant-MMAE conjugate, including the following steps:
(1) An rTRAIL mutant polymer is depolymerized and re-polymerized to generate an rTRAIL mutant trimer. This step particularly comprises: dissolving the rTRAIL mutant in a buffer containing zinc ion, adding tris(β-chloroethyl)phosphate (TCEP) thereinto, and reacting under water-bath for 1-3 hours at 30° C.-40° C.;

The aim of adding TCEP is to render the unstable polymer depolymerized to maintain in monomeric state, since polymer may be formed by disulfide bond between the rTRAIL mutants. Meanwhile, zinc ion in the reaction system can further promote the rTRAIL mutant monomers to form stable trimers.
(2) The rTRAIL mutant trimer is mixed with the MMAE having a linker to perform a coupling reaction. After coupling, each trimer may bind with 1-3 MMAE molecule(s); the coupling temperature preferably is 0-4° C. and the time is 30-60 min;
(3) After completion of the reaction, the rTRAIL mutant-MMAE conjugate is obtained by separation and purification;

Ultrafiltration tube with 10 kDa MWCO (Molecular Weight Cutoff) is sufficient to remove those small molecules in the system, because the molecular weight of the rTRAIL mutant-MMAE conjugate monomer of the present invention is 23 kDa and that of all other molecules in the reaction system is less than 10 kDa. Then, precipitation was removed by centrifugation to give a supernatant, which is further sterilized by filtration to obtain the conjugate of the present invention.

TRAIL molecule for mutation may be derived from a human or animal, preferably the natural human-derived TRAIL molecules, as they are more helpful for treatment of human tumor. It has been shown that the cysteine sulfhydryl groups are also present on the surface of natural rTRAIL monomer molecules, all of which are used to form stable trimers. The conjugating site is lost, however, for there are no free sulfhydryl groups on the surface of the trimer molecules. As a result, PCR site-directed mutation is adopted in the present invention to give an rTRAIL mutant comprising a cysteine mutation site, including the following steps:
(1) Total RNA was extracted from human tissues, which is taken as a template for reverse transcription to obtain a cDNA library;
(2) Primers P1 and P2 were utilized for PCR amplification with said cDNA as template to obtain a TRAIL coding sequence;
(3) Primers P3 and P4 were utilized for PCR site-directed mutation amplification with said TRAIL coding sequence as a template to obtain a mutated sequence;
(4) Said mutated sequence was operably connected into a vector to transform host cells;
(5) Transformed host cells were induced to express a fusion protein to obtain said rTRAIL mutant.

Sequences of said primers P1 and P2 are as follows:

```
P1:
                                       (SEQ ID NO: 5)
5'-ATGGCTATGATGGAGGTCCAGG-3';

P2:
                                       (SEQ ID NO: 6)
5'-TTAGCCAACTAAAAAGGCCCCG-3';
```

Sequences of said primers P3 and P4 are as follows:

```
P3:
                                       (SEQ ID NO: 7)
5'-TATACCATGGGCACCTCTGAGGAAACCATT

TCTACAGTTCAAGAAAAGCAACAATGTATTTCT-3';

P4:
                                       (SEQ ID NO: 8)
5'-TTCTCGAGTTAGCCAACTAAAAAGGCCCC

GAAAAAACTGGCTTCATGGTCCATGTCCATGTC-3'.
```

In another aspect, the present invention provides a use of said rTRAIL mutant-MMAE conjugate in preparation of anti-tumor drugs.

Said anti-tumor drugs contain an effective amount of said rTRAIL mutant-MMAE conjugate and at least one pharmaceutically acceptable carries, diluents or excipients. Usually, an active ingredient is mixed with excipients, or diluted with excipients, or may be encapsulated in carriers that can be present in a form of a capsule or a sachet in preparation. When the excipients work as diluents, solid, semi-solid or liquid substances may be adopted as the excipients, carriers or media of the active ingredient. Thus, a composition may be present in dosage forms of tablet, pill, powder, solution, syrup and sterilized injection etc.

Suitable excipients include lactose, glucose, sucrose, sorbitol, mannitol, starch, microcrystalline cellulose, polyvinyl pyrrolidone, cellulose, water and the like. The preparation may also include wetting agent, emulsifier, preservative (e.g., methyl hydroxybenzoate and propyl hydroxybenzoate), sweetener and the like. Said anti-tumor drugs may be prepared into a unit dosage form or multiple-unit dosage form, each dosage form comprising suitable pharmaceutically acceptable excipients and said rTRAIL mutant-MMAE conjugate in a predetermined amount that is calculated for expected efficacy.

Said anti-tumor drugs may be administered in the conventional way, including, but not limited to, intramuscularly, intraperitoneally, intravenously, subcutaneously, intradermally and locally etc.

When using said drugs, a safe and effective amount of said rTRAIL mutant-MMAE conjugate is administered to human preferably in the range of 0.5-50 mg/kg body weight (BW), more preferably 1-10 mg/kg BW. Of course, the administration route, the health status of the patient and other factors should be considered to determine the specific dose, all of which are within the ability of a skilled physician.

In addition, said rTRAIL mutant-MMAE conjugate of the present invention can be used in combination of other drugs, including but not limited to, various types of cytokines such as IFN, TNF, IL-2; various types of tumor chemotherapeutic drugs, for example, the drugs affecting nucleic acid biosynthesis such as 5-FU and methotrexate; alkylating agents such as nitrogen mustard and cyclophosphamide; transcription interfering & RNA synthesis preventing drugs such as adriamycin and actinomycin D; drugs affecting protein synthesis such as vincristine and camptothecin and some hormone drugs etc.

Compared with the prior art, the advantageous effects of the present invention are presented as follows:
(1) Said conjugate of the present invention has the biological functions of both rTRAIL mutant and MMAE, including both the ability of the rTRAIL mutant in inducing apoptosis outside tumor cells, and the ability of MMAE in inducing apoptosis by inhibiting tubulin in cells. Under the cooperation of the two, anti-tumor efficacy will be enhanced significantly.
(2) As the rTRAIL mutant binds with death receptors on the surface of tumor cells specifically, said conjugate of the present invention transport MMAE to the tumor cells directionally, which further is released inside tumor cells to play its role, not only killing the tumor cells with low-sensitivity and even resistance to TRAIL, but also reducing the toxic side effects caused by administration of MMAE alone.
(3) After the rTRAIL mutant in the conjugate of the present invention is coupled with MMAE, its water solution has better stability than that of rTRAIL molecule alone, showing no precipitation after repeated freezing and thawing.

DETAILED DESCRIPTION

The present invention is further illustrated in detail hereinafter with reference to the accompanying drawings and the embodiments.

1. Establishment of Human Prostate cDNA Library
(1) Extraction of Total mRNA from Human Prostate Frozen small pieces of human prostate tissue (about 100 mg) were ground in liquid nitrogen into powders, into which TRIZOL reagent (1 mL) was added to grind repeatedly, and transferred to 1.5 ml RNase-free eppendorf (EP) tube. The tube was placed at room temperature for 5 min, followed by addition of 0.2 mL chloroform to shake vigorously for 15 s and placed at room temperature for 3 min. Centrifuge at 4° C. for 15 min at 12000 g. The upper aqueous phase was transferred into another RNase-free EP tube. Isopropanol (0.5 mL) was added and kept at room temperature for 10 min to precipitate RNA. Centrifuge at 4° C. for 10 min at 12000 g and the supernatant was removed. The precipitate obtained was washed with 75% ethanol. Centrifuge at 4° C. for 5 min at 12000 g and remove the supernatant. The pellet was dried and then dissolved with 50 μL DEPC water, and stored at −70° C.

(2) Reverse Transcription (RT) PCR

With oligodT as a primer, human prostate total RNA as a template, AMV reverse transcriptase was added to conduct Reverse-PCR to obtain a cDNA library, including the following steps:

1) RNA pre-denaturation: 5 μg human prostate RNA+25 μg OligodT was made up to 10 μL with 01% DEPC, and subjected to 70° C. water-bath for 5 min and cooled to room temperature to destroy the secondary structure of mRNA.

2) RT: the synthesis system was as follows:

| Ingredient | Volume |
| --- | --- |
| Said RNA mixed solution | 10 μL |
| dNTP (each10 mM) | 3 μL |
| RNase inhibitor (40 U/μL) | 20 U |
| Reverse transcriptase | 15 U |
| 5 × Buffer | 4 μL |
| 0.1% DEPC | Make up to 20 μL |

| The PCR program was: reverse transcription process | 42° C. | 60 min |
| --- | --- | --- |
| inactivation of reverse transcriptase | 70° C. | 10 min |

The obtained cDNA was stored at −20° C. for later use.

2. Obtaining TRAIL Coding Sequence

With said cDNA as a template, P1 and P2 as the upstream and downstream primers, the coding sequence of TRAIL was synthesized and amplified under the catalysis of Taq DNA polymerase. Sequence analysis confirmed that the DNA sequence obtained was identical with the TRAIL coding sequence registered in GenBank (NM_003842.4), i.e., the TRAIL coding sequence was obtained. The sequences of the primers were as follows:

P1:
(SEQ ID NO: 5)
5'-ATGGCTATGATGGAGGTCCAGG-3';

P2:
(SEQ ID NO: 6)
5'-TTAGCCAACTAAAAAGGCCCCG-3'.

The PCR reaction system was as follows:

| Ingredients | Volume |
| --- | --- |
| 5 × PCR buffer (containing magnesium ions) | 10 μL |
| dNTP Mixture (each 2.5 mM) | 4 μL |
| P1 | 1 μL |
| P2 | 1 μL |
| cDNA | 2 μL |
| Prime Star High-Fidelity enzyme (2.5 U/μL) | 0.5 μL |
| ddH$_2$O | 31.5 μL |

The PCR reaction program is as follows:

| | | | |
| --- | --- | --- | --- |
| Pre-denaturation | 95° C. | 3 min | |
| Denaturation | 95° C. | 30 seconds | |
| Annealing | 55° C. | 30 seconds | 30 cycles |
| Extension | 72° C. | 1 min | |
| Extension | 72° C. | 10 min | |
| Hold | 4° C. | hold | |

3. Obtaining Mutant Sequence of TRAIL 95-281 (rTRAIL)

(1) Obtaining Mutant Sequence of rTRAIL N109C

With the TRAIL coding sequence as a template, P3 and P4 as the upstream and downstream primers, the coding sequence of rTRAIL N109C mutant was synthesized and amplified under the catalysis of Taq DNA polymerase. Sequence analysis confirmed that the DNA sequence obtained was shown in SEQ ID No.2, which was consistent with expectation. The sequences of the primers were as follows:

P3:
(SEQ ID NO: 7)
5'-TATACCATGGGCACCTCTGAGGAAACCATT

TCTACAGTTCAAGAAAAGCAACAATGTATTTCT-3';

P4:
(SEQ ID NO: 8)
5'-TTCTCGAGTTAGCCAACTAAAAAGGCCCC

GAAAAAACTGGCTTCATGGTCCATGTCCATGTC-3'.

Except for the primers and the template, the PCR reaction system and program were the same as that of step 2.

(2) Obtaining Mutant Sequence of rTRAIL S96C

With the TRAIL coding sequence as a template, P5 and P6 as the upstream and downstream primers, the coding sequence of rTRAIL N109C mutant was synthesized and amplified under the catalysis of Taq DNA polymerase. Sequence analysis confirmed that the DNA sequence obtained was shown in SEQ ID No.4, which was consistent with expectation. The sequences of the primers were as follows:

P5:
(SEQ ID NO: 9)
5'-TATACCATGGGCACCTGTGAGGAAACCATT

TCTACAGTTCAAGAAAAGCAACAAAATATTTCT-3';

P6:
(SEQ ID NO: 10)
5'-TTCTCGAGTTAGCCAACTAAAAAGGCCCC

GAAAAAACTGGCTTCATGGTCCATGTCCATGTC-3'.

Except for the primers and the template, the PCR reaction system and program were the same as that of step 2.

Hereinafter, the rTRAIL N109C mutant sequence was taken as an example to further illustrate preparation of rTRAIL mutant and construction of conjugates. The preparation of rTRAIL S96C mutant and construction of conjugates were the same.

4. Construction of Expression Vector Comprising the rTRAIL Mutant Sequence

The rTRAIL N109C mutant sequence and pET28a(+) were double-digested with NcoI/XhoI respectively, and then were ligated at a molar ratio of 3:1 with T4 ligase (Takara). The ligation products were transformed into E. coli DH5a competent cells, and positive clones were selected and cultured. After extraction of the plasmid, NcoI/XhoI double-digestion was used to verify their ligation, and sequencing was used to make further verification, resulting in that rTRAIL mutant expression vectors were obtained: pET28a (+)-rTRAIL N109C.

5. Transformation of Expression Vector into E. Coli to Establish Engineered Bacteria The expression vector pET28a(+)-rTRAIL N109C was transformed into E. coli expression host BL21 (DE3) (purchased from Novagen), and monoclone was picked from kanamycin plate and cultured overnight at 37° C., 160 rpm. The bacterial liquid PCR method was used to determine whether the rTRAIL mutant expression vector had been transformed into the expression host. With bacterial liquid as a template, P3 and P4 as primers, PCR was performed. Verified positive monoclones were identified as the engineered bacteria of interest, and the bacterial liquid was kept at −80° C. after addition of 10-15% glycerol.

6. Preparation and Purification of rTRAIL Mutant

The constructed engineered bacteria were inoculated in LB culture medium (200 mL, containing 15 μg/mL kanamycin), cultured in a shaker with a rotating speed of 160 rpm at 37° C. until the bacterial liquid OD600 reached about 0.8. IPTG (final concentration: 1 mM) was added to induce BL21 (DE3) to express fusion protein, with an induction time of 12 h. BL21 bacteria were obtained by centrifuging at 7200 g for 10 min.

Said bacteria was resuspended with loading buffer A and disrupted by a French press. After 7200 g centrifugation for 30 min, the supernatant was filtered through a 0.22 μm water membrane and was subjected to metal affinity chromatography with a Ni-NTA affinity column (GE). Imidazole (10 mM) was used to elute other proteins as impurities, and imidazole (60 mM) was used to get target protein. The fraction eluted with imidazole (60 mM) was treated by a desalinization column (GE) to change its buffer to buffer B, which was further subjected to ion exchange chromatography with a SP strong cation exchange column (GE). Buffer C was used for eluting the protein on the ion exchange column.

Wherein, the ingredients of each buffer were as follows:
Buffer A: 50 mM NaH$_2$PO$_4$, 300 mM NaCl, pH 7.4
Buffer B: 20 mM NaH$_2$PO$_4$, pH 6.0
Buffer C: 20 mM NaH$_2$PO$_4$, 1 M NaCl, pH 6.0

Figure 1:
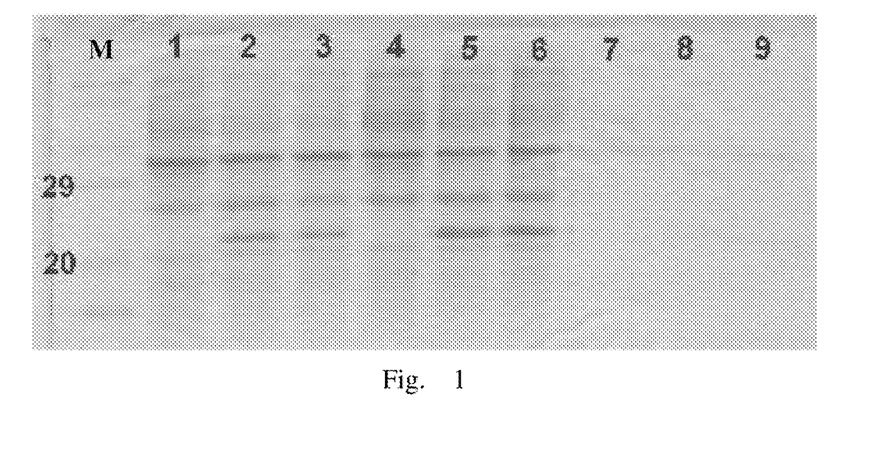
FIG. 1 is the electrophoretogram of rTRAIL mutant N109C expressed by *E. coli*. M is the low molecular weight marker; lane 1 is the non-induced bacterial liquid; lanes 2 and 3 are the induced bacterial liquid; lane 4 is the supernatant (soluble fraction) obtained by centrifuging lysed non-induced bacterial liquid; lanes 5 and 6 are the supernatant (soluble fraction) obtained by centrifuging lysed induced bacteria; lanes 7, 8 and 9 are the samples of induced and non-induced precipitation reconstituted with 8M urea.
Figure 2:
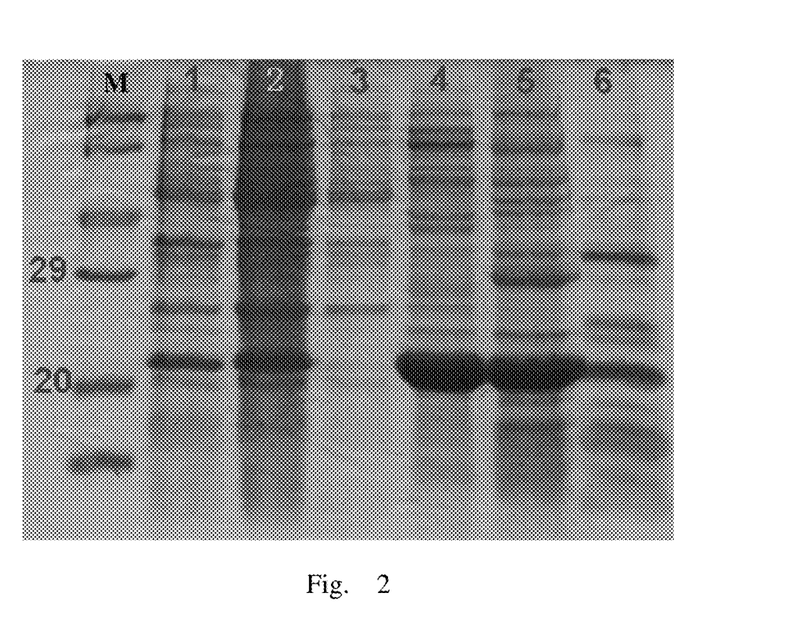
FIG. 2 is the electrophoretogram showing the affinity purification result of rTRAIL mutant N109C. M is the protein molecular weight marker; lane 1 is the bacterial liquid induced with IPTG; lane 2 is the supernatant after lysing the bacteria; lane 3 is the flow-through of Ni column; lane 4 is the eluate of imidazole (10 mM); lane 5 is the eluate of imidazole (60 mM); lane 6 is the eluate of imidazole (500 mM).
Figure 3:
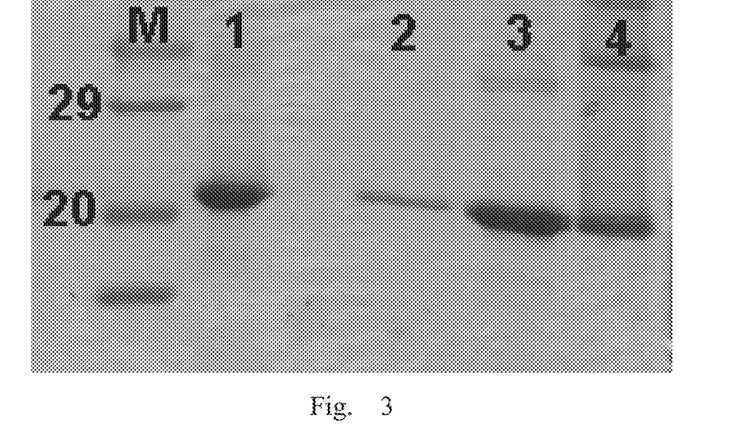
FIG. 3 is the electrophoretogram showing the SP strong cation exchange column purification result of rTRAIL mutant N109C. Lane 1 is the protein solution desalted with an imidazole eluent (10 mM); lanes 2 and 3 are the protein eluted with SP column, namely purified N109C; lane 4 shows the result of non-denaturing electrophoresis of N109C.

FIG. 1, FIG. 2 and FIG. 3 illustrated the electrophoretogram of prokaryotic expression and purification of the rTRAIL N109C mutant. As shown in FIG. 1, the rTRAIL N109C mutant achieved soluble expression in E. coli successfully. As shown in FIG. 2, the rTRAIL N109C mutant began to be eluted with imidazole (10 mM), and its purity was no less than 85% after preliminary purification. As shown in FIG. 3, part of other proteins could be removed after purification by SP column, yet 3 slight undesired bands were found. Meanwhile, according to the results of non-denaturing gel electrophoresis, dimmers, tetramers etc were still found in the substantially purified rTRAIL N109C mutant, which was caused by the disulfide bond between the mutant protein molecules.

The amino acid sequence of the N109C mutant obtained is shown in SEQ ID No.1, and the amino acid sequence of the S96C mutant obtained is shown in SEQ ID No.3.

7. Conjugation of rTRAIL Mutant and MMAE 0.5 mg rTRAIL N109C mutant was dissolved in 0.8 mL PBS (pH 6.0, containing 10 μM ZnCl$_2$), into which 6 μL TCEP was added, and water bath was maintained for 2 hours at 37° C. While stirring, 10-fold excessive amount of vcMMAE dissolved with 50 μL 30% acetonitrile/water was added to react at 4° C. for 40 min, and the reaction was ended by addition of excessive amount of cysteine. (Said vcMMAE was synthesized by Jiangyin Concortis Biotechnology Co., Ltd, and 10-fold excessive amount meant that the molar quantity of vcMMAE was greater than or equal to 10-fold of that of N109C in the reaction system.) Ultrafiltration tube with 10 kDa MWCO (Millipore) was used to remove the small molecules in the reaction system. The obtained conjugate was filtered through 0.22 μm (pore size) water membrane to remove bacteria and stored at −20° C. for later use.

Figure 4:
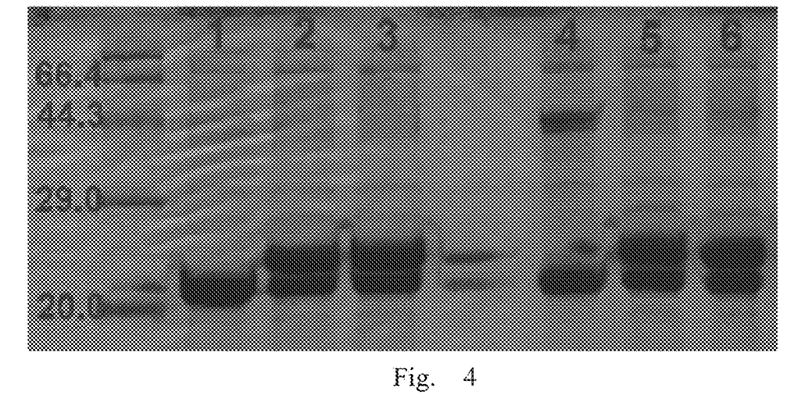
FIG. 4 is the electrophoretogram of N109C and its MMAE conjugate. Lane 1 is N109C; lane 2 is the N109C-vcMMAE conjugate; lane 3 is the desalted N109C-vcMMAE conjugate; lanes 4, 5 and 6 show the electrophoresis results of the samples in lanes 1, 2, and 3 under non-denatured condition, respectively.
Figure 5:
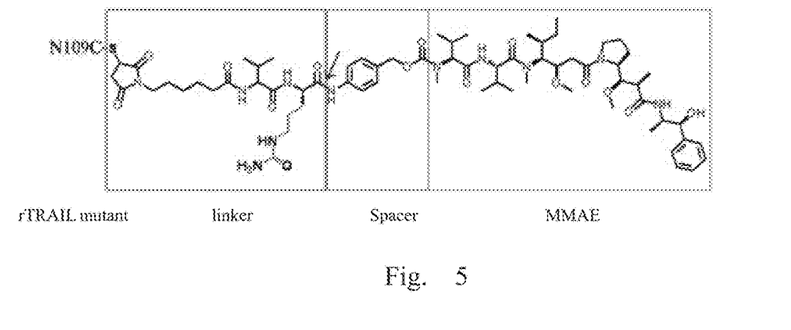
FIG. 5 is the schematic diagram showing the connection relationship among various portions of the rTRAIL mutant-vcMMAE conjugate.

FIG. 4 illustrated the electrophoretogram for the conjugate of N109C and MMAE. As shown in this figure, the protein band apparently shifted after a conjugate was formed, indicating that the small molecule, MMAE, had been conjugated to the protein, such that the electrophoretic behavior thereof was changed. By comparing lane 1 with lane 4, it can be seen that polymers existed since one cysteine residue was mutated in N109C. Further, by comparing lane 3 with lane 6, during conjugation, the rTRAIL N109C polymer was depolymerized by TCEP, and the zinc ion facilitated N109C monomer to form a stable trimer. Between its cysteine sulfhydryl group and the maleimide group of vcMMAE, an alkylation reaction took place to generate conjugates coupled with different numbers of MMAE. The connection relationship among various portions of the rTRAIL mutant-vcMMAE conjugate was shown in FIG. 5.

8. Measurement of In Vitro Anti-Tumor Activity of the Conjugate 4 types of cells were selected to measure in vitro anti-tumor activity of the rTRAIL mutant and the MMAE conjugate: TRAIL sensitive type (NCI-H460), TRAIL insensitive type (Hela), TRAIL resistant type (MCF-7) and normal cells (HEK293). All of these 4 types of cells had TRAIL death receptor on their surfaces.

Hereinafter, TRAIL sensitive type NCI-H460 cell was taken as an example to give detailed description of the test procedure, including the following steps:

(1) Digesting the NCI-H460 cells into individual cells, followed by diluting to 1×10$^4$ cells/mL, spreading the cells on 96-well plate (100 μL for each well), and culturing the cells for 24 hours under normal condition.

(2) Diluting N109C, N109C-vcMMAE and S96C-vcMMAE with culture medium respectively, and adding them into the cell plate with final concentrations of 32, 63, 125, 250, 500, 1000 ng/mL for serving as the test groups, while using standard TRAIL (114-281) as the positive control group, using the buffer (used for dissolving the test sample, diluted with the culture medium in a same manner) as the negative control group, and using the culture medium (without adding any solution) as the blank control group. All the control groups and test groups were tested in triplicate.

(3) Adding the sample in control group and test group into the cell plate, culturing for 96 hours at 37° C., and observing the killing ability on target cells of the control group and test group.

(4) Adding 10 μL CCK-8 color-developing solution into each well after completion of the culture, incubating the samples for color-developing for 1 hour in an incubator, and taking them out to measure at dual-wavelength of 450 nm and 630 nm.

(5) Calculation of result: the samples in the test group having an OD value greater than the one of equivalent dilution in the negative group were deemed as positive (t-test, P<0.01). The calculation result was shown in FIG. 6.

Figure 6:
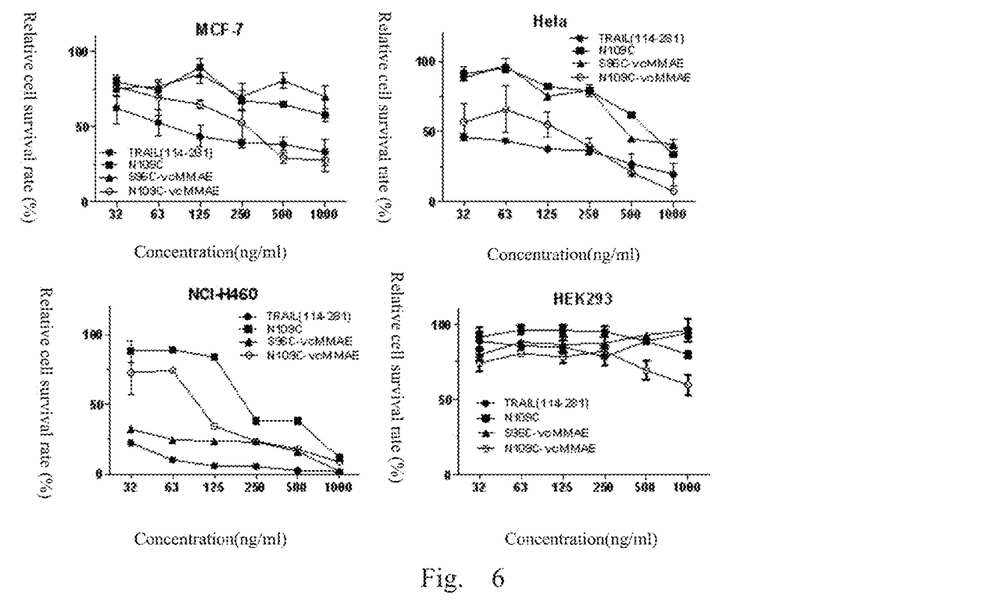
FIG. 6 shows the killing effect of various TRAIL elements on different cell lines.

As shown in FIG. 6, as for the four different cells, the rTRAIL mutant-vcMMAE conjugate always exhibited stronger killing ability to tumor cells than the rTRAIL mutant.

As for NCI-H460 cells, the activities of the rTRAIL mutant and its MMAE conjugate were not better than that of TRAIL (114-281).

As for Hela and MCF-7 cells, the rTRAIL mutant-vcMMAE conjugate showed stronger killing ability at higher concentration, but was slightly weaker than TRAIL (114-281) at lower concentration (<250 ng/mL). It was likely that the rTRAIL mutant-vcMMAE conjugate endocytosed by cells did not accumulate sufficient amount of MMAE to induce apoptosis at lower concentration. Thus, higher concentration brought better killing effect. Nevertheless, N109C-vcMMAE had stronger killing ability than S96C-vcMMAE at both low and high concentrations.

As for the normal HEK293 cells, all of TRAIL (114-281), the rTRAIL mutant and its MMAE conjugate were confirmed to have considerably low toxicity.

9. Distribution of the Conjugate in Tumor-Bearing Animal Model

N109C-vcMMAE was taken as an example, and the conjugate was tracked in real-time in mice by Fluorescent labeling method to observe tumor targeting ability of the conjugate.

(1) Establishment of Tumor-Bearing Animal Model

Athymic mice weighing 20 g were selected and 10$^7$ NCI-H460 cells were injected subcutaneously in the armpit of one side of the forelegs. 3 days later, tumor formation can be clearly observed.

(2) Fluorescent Labeling of the Conjugate

Cy5, as a Near-IR-activated dye, was used as a fluorescent label, so as to facilitate the fluorescence to pass through animal skin and achieve the goal of real time vital observation. In terms of concrete method of Cy5 labeling, please refer to the instruction offered by the manufacturer (Lumiprobe).

(3) Administration and Real Time Observation

200 μL sample containing about 50 μg Cy5-labeled conjugate was injected into the tumor-bearing mice via tail vein, while equal amount of normal saline was injected into the blank control group.

Small living animal imager (NightOWLN320) was used to observe distribution of fluorescence in mice every 24 hours. Before observation, after 12 hours fasting, the mice were anesthetized with ether and observed successively for 4 days until systemic fluorescence of the mice disappeared totally. The mice were killed after 4th day, and heart, liver, spleen, lung, kidney and tumor tissues were isolated. Specific distribution of the conjugate in each tissue of animals in test group was confirmed by small living animal imager. The imaging result was shown in FIG. 7. The white arrow indicates tumor site.

Figure 7:
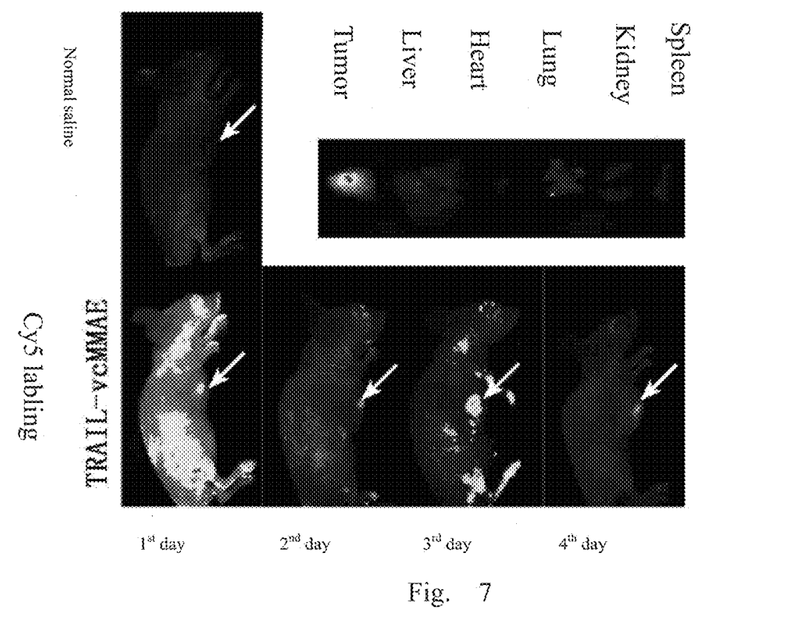
FIG. 7 is the distribution of N109C-vcMMAE conjugate in tumor-bearing mice.

As shown in FIG. 7, most of the fluorescence had gathered on tumor site at 3rd day, and only the tumor site emitted fluorescence at 4th day. After killing the animals, the result by fluorescence detection was consistent with that detected in vivo and in real time, showing that N109C-vcMMAE had excellent tumor-targeting effect.

10. Research on Molecular Mechanism of the Conjugate for Anti-Tumor Activity

NCI-H460 cells were taken as an example to observe behaviors of rTRAIL mutant-vcMMAE conjugate in tumor cells by laser confocal technology, including the following steps:

a) A coverslip was immersed with 1M HCl and 70% ethanol, subjected to ultrasonic treatment for 30 min, washed for 5-6 times with double distilled water and sterilized for later use;
b) Well-sterilized coverslip was placed in 24-well plate, and cells were plated at $10^4$ cells/well and cultured overnight at 37° C.;
c) Administration: N109C-vcMMAE and S96C-vcMMAE were diluted respectively to a final concentration of 1 μg/mL, and the cells were treated according to step d) at different time points ($1^{st}$, $4^{th}$, $8^{th}$ and $12^{th}$ hour), while drug-free culture medium was used for the blank control group;
d) The coverslip was washed with cold PBS for 3 times and then fixed with 4% paraformaldehyde for 10 min at room temperature;
e) PBS was used to wash the coverslip for another 3 times;
f) 0.1% Triton X-100 was added to permeabilize for 10 min at room temperature;
g) 2% BSA was added to block for 30 min after 3 times washing with PBS;
h) Primary antibody incubation: rabbit anti-human rTRAIL polyclonal antibody was diluted with 1% BSA/PBS to 1 μg/mL and incubated for 45 min at room temperature;
i) Secondary antibody incubation: FITC-labeled goat anti-rabbit secondary antibody was diluted 500-fold with 1% BSA/PBS and incubated for 45 min at room temperature;
j) Staining cell nucleus with DAPI: after PBS washing (3 times), DAPI diluted 1000-fold with PBS was added drop-wise on each coverslip (it was appropriate to just cover the cells), and the coverslip was incubated for about 2 min at 25° C.;
k) Mounting: after PBS washing, one drop of Anti-fade Fluorescence Mounting Medium was added on the coverslip, then the coverslip was placed upside down on a glass slide and then sealed with nail polish around the coverslip;
l) Cofocal detection: the detection result was shown in FIG. 8.

Figure 8:
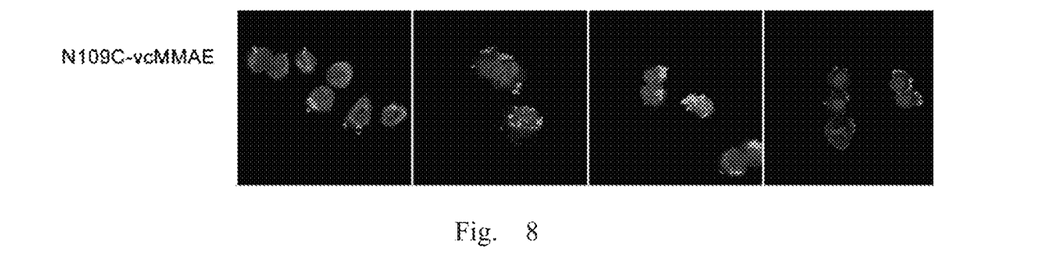
FIG. 8 is a photomicrograph showing the experiment of cell endocytosis of N109C-vcMMAE conjugate by tumor cells.

FIG. 8 shows the cell nucleus and the rTRAIL mutant-vcMMAE conjugates with fluorescence. 1 hour after administration, a lot of N109C-vcMMAE had entered the cells. 4 hours later, more and more N109C-vcMMAE entered the cells and began to aggregate slowly. 8 hours later, there were more aggregating points emerging inside the cells. 12 hours later, the aggregating points inside the cells decreased gradually and cell apoptosis began to occur, evidenced by heterogeneity in cell nucleus.

Figure 9:
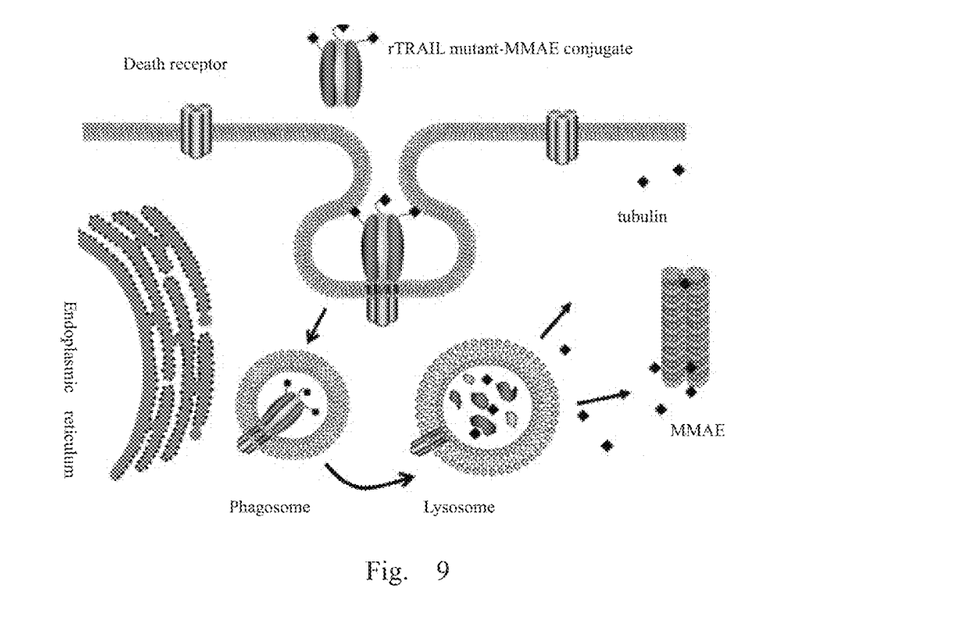
FIG. 9 is the schematic diagram showing the apoptosis-inducing mechanism of the rTRAIL mutant-vcMMAE conjugate.

We could conclude that the action mechanism of said rTRAIL mutant-vcMMAE conjugates is: the conjugates bind with dearth receptors on the surface of tumor cells through the rTRAIL mutants, and are endocytosed by tumor cells to form a phagosome, which will further be fused with lysosomes. The dipeptide linker arm in the conjugate is hydrolysed by lysosomal cathepsin to release MMAE, which will then play its role in tumor cells, i.e., inducing apoptosis by inhibiting dimerization of tubulin. Its apoptosis-inducing mechanism is shown in FIG. 9.

The invention claimed is:

1. An rTRAIL mutant, characterized in that the amino acid sequence is represented by SEQ ID No.1.

2. A gene encoding the rTRAIL mutant according to claim 1, characterized in that the base sequence is represented by SEQ ID NO.2.

3. The polynucleotide of claim 2 in operable association with a promoter, or a recombinant vector or an expression system containing the polynucleotide according to claim 2.

4. An rTRAIL mutant-MMAE conjugate, characterized in that it is formed by conjugating monomethyl auristatin E (MMAE) with an rTRAIL mutant trimer through a linker, the amino acid sequence of the rTRAIL mutant is represented by SEQ ID No.1, and said linker is a maleimide-modified valine-citrulline dipeptide.

5. An use of the rTRAIL mutant-MMAE conjugate according to claim 4 in preparation of anti-tumor drugs.

6. A method of preparing an rTRAIL mutant-MMAE conjugate, comprising:

(1) An rTRAIL mutant polymer is depolymerizd and re-polymerized to generate an rTRAIL mutant trimer;

(2) The rTRAIL mutant trimer is mixed with a MMAE having a linker to perform a coupling reaction;

(3) After completion of the reaction, the rTRAIL mutant-MMAE conjugate is obtained by separation and purification;

wherein, the amino acid sequence of the rTRAIL mutant is represented by SEQ ID No.1;

said linker is a maleimide-modified valine-citrulline dipeptide.

7. The method according to claim 6, wherein said rTRAIL mutant trimer is prepared by a method comprising:

dissolving the rTRAIL mutant in a buffer containing zinc ion, adding tris(β-chloroethyl) phosphate thereinto, and reacting under water-bath for 1~3 hours at 30° C.~40° C.

8. The method according to claim 6, wherein said coupling reaction is performed at a temperature of no higher than 4° C. for 30~60 min.

9. The method according to claim 6, wherein said separation and purification includes: removing the substances with molecular weights below 10 kDa from the reaction solution by ultrafiltration, removing the precipitate by centrifugation to give a supernatant, and sterilizing the supernatant by filtration to obtain the rTRAIL mutant-MMAE conjugate.

\* \* \* \* \*

UNITED STATES PATENT AND TRADEMARK OFFICE
CERTIFICATE OF CORRECTION

PATENT NO. : 9,617,326 B2
APPLICATION NO. : 14/437987
DATED : April 11, 2017
INVENTOR(S) : Shuqing Chen It is certified that error appears in the above-identified patent and that said Letters Patent is hereby corrected as shown below:

In the Claims

Please replace "An" with -- A -- in Claim 1 (Column 17, Line 46).

Please replace "gene" with -- polynucleotide -- in Claim 2 (Column 17, Line 48).

Please replace "NO.2" with -- No.2 -- in Claim 2 (Column 17, Line 50).

Please replace "An" with -- A -- in Claim 4 (Column 17, Line 54).

Please replace "an" with -- a -- in Claim 4 (Column 17, Line 56).

Please replace "An use of" with -- A method for treating a tumor comprising the step of administering a therapeutically effective amount of -- in Claim 5 (Column 17, Line 60).

Please replace "in preparation of anti-tumor drugs" with -- to a subject in need thereof -- in Claim 5 (Column 17, Line 61).

Please replace Claim 6 with the following:
-- A method of preparing a rTRAIL mutant-MMAE conjugate, comprising:
    (1) Depolymerizing and re-polymerizing a rTRAIL mutant polymer to generate a rTRAIL mutant trimer in the presence of tris(β-chloroethyl) phosphate;
    (2) Mixing the rTRAIL mutant trimer with a MMAE having a linker to generate a reaction solution, and performing a coupling reaction on the reaction solution to generate the rTRAIL mutant-MMAE conjugate;
    (3) Obtaining the rTRAIL mutant-MMAE conjugate after completion of the coupling reaction by separation and purification from the reaction solution of step (2);

Signed and Sealed this
Fourth Day of September, 2018

Andrei Iancu
*Director of the United States Patent and Trademark Office*

CERTIFICATE OF CORRECTION (continued)
U.S. Pat. No. 9,617,326 B2 wherein,
the amino acid sequence of the rTRAIL mutant is represented by SEQ ID No.1;
said linker is a maleimide-modified valine-citrulline dipeptide. -- (Column 17, Line 62 to Column 18, Line 53).

Please insert the following phrase -- depolymerizing and re-polymerizing the rTRAIL mutant polymer to generate -- after "wherein" in Claim 7 (Column 18, Line 54).

Please replace "prepared" with -- accomplished -- in Claim 7 (Column 18, Line 55).

Please replace "ion" with -- ions -- in Claim 7 (Column 18, Line 57).

SEQUENCE LISTING

```
<160> NUMBER OF SEQ ID NOS: 10

<210> SEQ ID NO 1
<211> LENGTH: 187
<212> TYPE: PRT
<213> ORGANISM: Artificial Sequence
<220> FEATURE:
<223> OTHER INFORMATION: Synthetic polypeptide

<400> SEQUENCE: 1

Thr Ser Glu Glu Thr Ile Ser Thr Val Gln Glu Lys Gln Gln Cys Ile
1               5                   10                  15

Ser Pro Leu Val Arg Glu Arg Gly Pro Gln Arg Val Ala Ala His Ile
            20                  25                  30

Thr Gly Thr Arg Gly Arg Ser Asn Thr Leu Ser Ser Pro Asn Ser Lys
        35                  40                  45

Asn Glu Lys Ala Leu Gly Arg Lys Ile Asn Ser Trp Glu Ser Ser Arg
    50                  55                  60

Ser Gly His Ser Phe Leu Ser Asn Leu His Leu Arg Asn Gly Glu Leu
65                  70                  75                  80
```

Val Ile His Glu Lys Gly Phe Tyr Tyr Ile Tyr Ser Gln Thr Tyr Phe
                85                  90                  95

Arg Phe Gln Glu Glu Ile Lys Glu Asn Thr Lys Asn Asp Lys Gln Met
            100                 105                 110

Val Gln Tyr Ile Tyr Lys Tyr Thr Ser Tyr Pro Asp Pro Ile Leu Leu
        115                 120                 125

Met Lys Ser Ala Arg Asn Ser Cys Trp Ser Lys Asp Ala Glu Tyr Gly
130                 135                 140

Leu Tyr Ser Ile Tyr Gln Gly Gly Ile Phe Glu Leu Lys Glu Asn Asp
145                 150                 155                 160

Arg Ile Phe Val Ser Val Thr Asn Glu His Leu Ile Asp Met Asp His
                165                 170                 175

Glu Ala Ser Phe Phe Gly Ala Phe Leu Val Gly
            180                 185

<210> SEQ ID NO 2
<211> LENGTH: 561
<212> TYPE: DNA
<213> ORGANISM: Artificial Sequence
<220> FEATURE:
<223> OTHER INFORMATION: Synthetic oligonucleotide

<400> SEQUENCE: 2
acctctgagg aaaccatttc tacagttcaa gaaaagcaac aatgtatttc tcccctagtg    60
agagaaagag gtcctcagag agtagcagct cacataactg ggaccagagg aagaagcaac   120
acattgtctt ctccaaactc caagaatgaa aaggctctgg ccgcaaaat aaactcctgg    180 gaatcatcaa ggagtgggca ttcattcctg agcaacttgc acttgaggaa tggtgaactg   240
gtcatccatg aaaagggtt ttactacatc tattcccaaa catactttcg atttcaggag    300
gaaataaaag aaaacacaaa gaacgacaaa caaatggtcc aatatattta caaatacaca   360
agttatcctg accctatatt gttgatgaaa agtgctagaa atagttgttg gtctaaagat   420
gcagaatatg gactctattc catctatcaa gggggaatat ttgagcttaa ggaaaatgac   480 agaattttg tttctgtaac aaatgagcac ttgatagaca tggaccatga agccagtttt    540
ttcggggcct ttttagttgg c                                             561

<210> SEQ ID NO 3
<211> LENGTH: 187
<212> TYPE: PRT
<213> ORGANISM: Artificial Sequence
<220> FEATURE:
<223> OTHER INFORMATION: Synthetic polypeptide

<400> SEQUENCE: 3

Thr Cys Glu Glu Thr Ile Ser Thr Val Gln Glu Lys Gln Gln Asn Ile
1               5                   10                  15

Ser Pro Leu Val Arg Glu Arg Gly Pro Gln Arg Val Ala Ala His Ile
            20                  25                  30

Thr Gly Thr Arg Gly Arg Ser Asn Thr Leu Ser Ser Pro Asn Ser Lys
        35                  40                  45

Asn Glu Lys Ala Leu Gly Arg Lys Ile Asn Ser Trp Glu Ser Ser Arg
50                  55                  60

Ser Gly His Ser Phe Leu Ser Asn Leu His Leu Arg Asn Gly Glu Leu
65                  70                  75                  80

Val Ile His Glu Lys Gly Phe Tyr Tyr Ile Tyr Ser Gln Thr Tyr Phe
                85                  90                  95

```
Arg Phe Gln Glu Glu Ile Lys Glu Asn Thr Lys Asn Asp Lys Gln Met
                100                 105                 110

Val Gln Tyr Ile Tyr Lys Tyr Thr Ser Tyr Pro Asp Pro Ile Leu Leu
            115                 120                 125

Met Lys Ser Ala Arg Asn Ser Cys Trp Ser Lys Asp Ala Glu Tyr Gly
130                 135                 140

Leu Tyr Ser Ile Tyr Gln Gly Gly Ile Phe Glu Leu Lys Glu Asn Asp
145                 150                 155                 160

Arg Ile Phe Val Ser Val Thr Asn Glu His Leu Ile Asp Met Asp His
                165                 170                 175

Glu Ala Ser Phe Phe Gly Ala Phe Leu Val Gly
            180                 185

<210> SEQ ID NO 4
<211> LENGTH: 561
<212> TYPE: DNA
<213> ORGANISM: Artificial sequence
<220> FEATURE:
<223> OTHER INFORMATION: Synthetic oligonucleotide

<400> SEQUENCE: 4
acctgtgagg aaaccatttc tacagttcaa gaaaagcaac aaaatatttc tcccctagtg      60
agagaaagag gtcctcagag agtagcagct cacataactg ggaccagagg aagaagcaac     120
acattgtctt ctccaaactc caagaatgaa aaggctctgg ccgcaaaat aaactcctgg      180 gaatcatcaa gggagtgggca ttcattcctg agcaacttgc acttgaggaa tggtgaactg    240
gtcatccatg aaaagggtt ttactacatc tattcccaaa catactttcg atttcaggag      300
gaaataaaag aaaacacaaa gaacgacaaa caaatggtcc aatatattta caaatacaca     360
agttatcctg accctatatt gttgatgaaa agtgctagaa atagttgttg gtctaaagat     420
gcagaatatg gactctattc catctatcaa gggggaatat ttgagcttaa ggaaaatgac     480 agaattttttg tttctgtaac aaatgagcac ttgatagaca tggaccatga agccagtttt    540
ttcggggcct ttttagttgg c                                               561

<210> SEQ ID NO 5
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 5
atggctatga tggaggtcca gg                                              22

<210> SEQ ID NO 6
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 6
ttagccaact aaaaaggccc cg                                              22

<210> SEQ ID NO 7
<211> LENGTH: 63
<212> TYPE: DNA
<213> ORGANISM: Artificial sequence
<220> FEATURE:
```

```
<223> OTHER INFORMATION: Synthetic oligonucleotide

<400> SEQUENCE: 7
tataccatgg gcacctctga ggaaaccatt tctacagttc aagaaaagca acaatgtatt      60
tct                                                                    63

<210> SEQ ID NO 8
<211> LENGTH: 62
<212> TYPE: DNA
<213> ORGANISM: Artificial sequence
<220> FEATURE:
<223> OTHER INFORMATION: Synthetic oligonucleotide

<400> SEQUENCE: 8
ttctcgagtt agccaactaa aaaggccccg aaaaaactgg cttcatggtc catgtccatg      60
tc                                                                     62

<210> SEQ ID NO 9
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 9
tataccatgg gcacctgtga ggaaaccatt tctacagttc aagaaaagca acaaaatatt      60
tct                                                                    63

<210> SEQ ID NO 10
<211> LENGTH: 62
<212> TYPE: DNA
<213> ORGANISM: Artificial sequence
<220> FEATURE:
<223> OTHER INFORMATION: Synthetic oligonucleotide

<400> SEQUENCE: 10
ttctcgagtt agccaactaa aaaggccccg aaaaaactgg cttcatggtc catgtccatg      60
tc                                                                     62
```